United States Patent [19]

Blömer

[11] Patent Number: 4,863,444
[45] Date of Patent: Sep. 5, 1989

[54] ANTIBIOTIC-CONTAINING AGENT AND ITS USE AS A SURGICAL PLASTIC MATERIAL

[76] Inventor: Alois Blömer, Gildenstrasse 61, D-4390 Gladbeck, Fed. Rep. of Germany

[21] Appl. No.: 310,503

[22] Filed: Feb. 10, 1989

Related U.S. Application Data

[63] Continuation of Ser. No. 54,596, May 14, 1987, abandoned.

[30] Foreign Application Priority Data

Sep. 19, 1985 [DE] Fed. Rep. of Germany ....... 3533369

[51] Int. Cl.$^4$ .............................................. A61F 13/00
[52] U.S. Cl. .............................. 604/304; 128/92 YF; 128/92 V; 623/13; 604/265; 424/423
[58] Field of Search .......... 128/92 YF, 92 VP, 92 W, 128/334 R; 604/304, 309, 265, 93, 891; 623/13; 424/423, 426, 432, 444

[56] References Cited

U.S. PATENT DOCUMENTS

| | | | |
|---|---|---|---|
| 3,695,921 | 10/1972 | Shepherd | 427/2 |
| 3,805,300 | 4/1974 | Tascon-Alonso et al. | 623/13 |
| 3,882,858 | 5/1975 | Klemm | 128/92 R |
| 3,987,497 | 10/1971 | Stoy et al. | 623/13 |
| 4,191,743 | 3/1980 | Klemm | 424/28 |
| 4,297,993 | 11/1981 | Härle | 128/92 D |
| 4,329,743 | 5/1982 | Alexander et al. | 623/13 |
| 4,373,217 | 2/1983 | Draenert | 128/92 VP |
| 4,455,690 | 6/1989 | Homsy | 623/13 |
| 4,708,132 | 11/1987 | Silvestrini | 128/92 YF |
| 4,731,054 | 3/1988 | Billeter et al. | 604/265 |

FOREIGN PATENT DOCUMENTS

| | | | |
|---|---|---|---|
| 1183776 | 12/1985 | Canada | 167/205 |
| 0022289 | 1/1981 | European Pat. Off. | 604/265 |
| 2815934 | 10/1979 | Fed. Rep. of Germany | |

*Primary Examiner*—C. Fred Rosenbaum
*Assistant Examiner*—Mark O. Polutta
*Attorney, Agent, or Firm*—Herbert Dubno

[57] ABSTRACT

It is known that antibiotics, particularly gentamycine, are released with delay from plastic materials such as polymethacrylate and/or polyacrylate. Thereby, a steep initial decrease in concentration long periods of time. These antibiotic-containing synthetic materials have been used heretofore as bone cement, for the fastening of endoprostheses or in the, for instance of total endoprostheses of the hip or in the replacement of infected endoprostheses. To combat and prevent infection, the antibiotics are added prior to the polymerization of the synthetic material. The invention has the object to create. In accordance with the invention, it is the carrier (2) be shaped like a stick. The carrier (2) can also have the shape of a cylinder, with a central passage duct (4) provided in its longitudinal direction. The carrier (2) is provided with a plurality of radial openings (3), which communicate with a central passage duct (4).

6 Claims, 1 Drawing Sheet

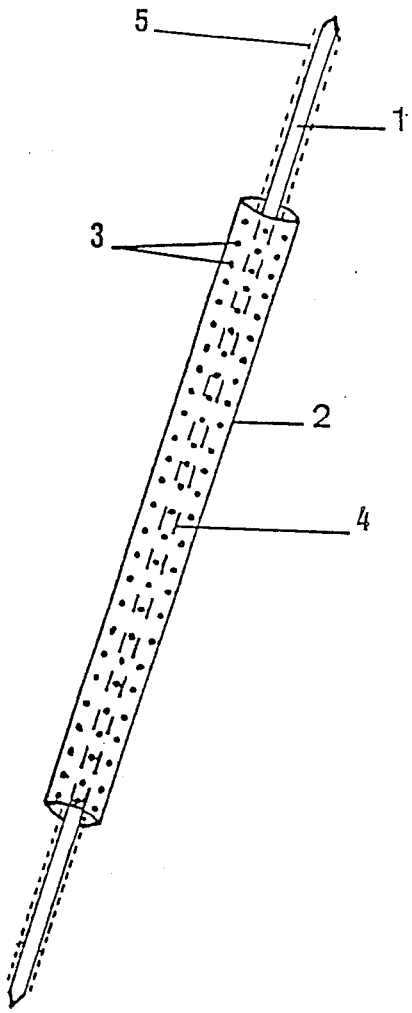

ANTIBIOTIC-CONTAINING AGENT AND ITS USE AS A SURGICAL PLASTIC MATERIAL

This is a continuation of co-pending application Ser. No. 054,596 filed on May 14, 1987, now abandoned.

It is known that antibiotics, particularly gentamycin, are slowly released from plastic materials of the polymethacrylate and/or polyacrylate type. After an initial steep decrease in concentration due to the release of the antibiotic contained in the outer layers of the synthetic material, there follows an almost constant release, slowly decreasing over a long period of time. These antibiotic-containing synthetic materials have been used up to now as bone cement, for the fastening of endoprostheses, for instance of total endoprostheses of the hip, or in the replacement of infected endoprostheses. In order to combat and prevent infection, the antibiotics are added to the plastic material prior to polymerization.

German Patent 23 20 373 discloses an antibiotic-containing agent, which has a spherical shape and wherein the antibiotic is evenly distributed in the plastic material. The balls have a diameter of 1-20 mm and are preferably connected to each other with the aid of threads or wires. This agent is used, for instance, in the filling of osteomyelitic cavities, or for an aspectic graft support, etc.

In the treatment of fractures, it is known to use a so-called external fixture. This consists of bones, nails or screws, which are introduced into the bone through the skin and the soft tissues, above and below the fracture. The external ends are connected to each other via tensioning elements. Due to the affected areas created in the soft tissues by the insertion of the bones, nails or screws, the danger of germ penetration into the soft tissue and bones arises, leading to inflammation.

Departing from this state of the art, the invention has the object to create an antibiotic-carrying agent of the kind described in the introduction, which is used during and after the application of such so-called external fixtures, in order to avoid complications.

In accordance with the invention, the carrier of the antibiotic-containing agent has the shape of a stick. Due to their elongated configuration, the carriers can be easily and simply inserted into the channels which are provided in the bones and the soft tissues, in order to accommodate the nails, pins and the like, which are used for the application of the external fixture.

Surprisingly it has been found that as a result of the introduction of the antibiotic-containing agent according to the invention, in the mentioned channels, the heretofore frequent complications such as infections of the nail channel and soft tissues occurring during the application of an external fixture could be widely avoided.

Advantageously, the carrier has a cylindrical shape, provided with a central longitudinal duct. This configuration is suited also for the insertion in the nail-channels in the case of starting infection or infection danger, as for instance in the case of open fractures. The carrier is slid over the fixation pin and inserted into the nail channel together therewith.

According to a further embodiment of the invention, the carrier is provided with a multitude of radial ducts. The carrier is slid over a fixation pin and introduced together therewith into a nail channel. The generated secretions can be diverted towards the outside between the outer circumference of the pin and the inner circumference of the carrier, through the capillary interstice therebetween.

However, it is also possible to mount the carrier as a fixed casing on a nail, pin of an external fixture or the like, here the carrier is introduced into the nail channel together with the fixation pin and remains in the channel during the time period the external fixture is applied.

An embodiment example of the invention is described in more detail with the aid of the drawing which shows in a diagrammatic fashion a fixation pin of an external fixture with a fixed shell, made of the carrier according to the invention.

BRIEF DESCRIPTION OF THE DRAWINGS

FIG. 1 is a perspective view illustrating a surgical nail in the sleeve.

Fixation pin 1 of an external fixture normally has a diameter of approx. 4 mm. Pin 1 is surrounded rigidly by carrier 2. The carrier 2 is provided circumferentially over its entire length with a plurality of radial outlet openings 3, which communicate with the central duct 4 of the carrier 2. Pin 1 is provided with the threading 5, in the usual manner. Carrier 2 has a diameter of approx. 5.6 mm.

The carrier 2 is made of synthetic material based on polymethacrylate and/or polyacrylate or similar materials. Gentamycin is preferably used as the antibiotic.

I claim:
1. Antibiotic delivery article comprising:
   a carrier in the form of a hollow elongate cylinder fabricated from a plastic material;
   a central passage duct within said cylinder aligned along a longitudinal axis thereof;
   a plurality of radial outlet openings formed in said carrier distributed over an entire length of said carrier and leading to an outer surface thereof, said openings communicating with said central passage duct;
   an antibiotic agent evenly and releasably distributed within said carrier; and
   a fixation means selected from the group consisting of nails, pins and screws inserted into and traversing a full length of said central passage duct.
2. An article according to claim 1 wherein the plastic material is formed from a polymer selected from the group consisting of polymethacrylate, polyacrylate and mixtures thereof.
3. An article according to claim 1 wherein said antibiotic is gentamycin.
4. A method for combatting infection arising from external fixtures, that includes fixation means selected from the group consisting of nails, pins and screws, inserted into a part of a human body, the method comprising surrounding said fixation means over a full length thereof by a carrier in the form of a hollow elongate cylinder fabricated from a plastic material, said carrier having a central passage duct aligned along a longitudinal axis of the carrier, a plurality of radial outlet openings formed in said carrier distributed over an entire length of said carrier and leading to an outer surface thereof wherein said openings communicate with said central passage duct, and an antibiotic agent evenly and releasably distributed within said carrier and disposing said carrier around said fixation means in said part of said human body.
5. A method according to claim 4 wherein the plastic material is formed from a polymer selected from the group consisting of polymethacrylate, polyacrylate and mixtures thereof.
6. A method according to claim 4 wherein said antibiotic is gentamycin.

* * * * *